United States Patent [19]

Kaler et al.

[11] Patent Number: 5,165,994
[45] Date of Patent: Nov. 24, 1992

[54] SPONTANEOUS EQUILBRIUM SURFACTANT VESICLES

[75] Inventors: Eric W. Kaler; A. Kamalakara Murthy; Beatriz E. Rodriguez, all of Newark, Del.

[73] Assignee: University of Delaware, Newark, Del.

[21] Appl. No.: 533,291

[22] Filed: Jun. 5, 1990

[51] Int. Cl.$^5$ .................. B01J 13/02; A61K 9/133
[52] U.S. Cl. .................. 428/402.2; 264/4.1; 424/450; 436/829
[58] Field of Search .................. 264/4.1, 4.33; 428/402.2, 402.21; 424/450; 436/829

[56] References Cited

U.S. PATENT DOCUMENTS

| | | | |
|---|---|---|---|
| 4,217,344 | 8/1980 | Vanlerberghe et al. | 264/4.1 X |
| 4,469,621 | 9/1984 | Kunitake et al. | 264/4.1 X |
| 4,619,794 | 10/1986 | Hauser | 264/4.1 |
| 4,670,185 | 6/1987 | Fujiwara et al. | 264/4.1 X |
| 4,743,449 | 5/1988 | Yoshida et al. | 264/4.1 X |
| 4,853,228 | 8/1989 | Wallach et al. | 424/450 |
| 4,861,502 | 8/1989 | Caswell | 252/174.25 X |
| 4,911,928 | 3/1990 | Wallach | 264/4.1 X |
| 5,030,442 | 7/1991 | Uster et al. | 264/4.1 X |
| 5,032,457 | 7/1991 | Wallach | 428/402.2 |

OTHER PUBLICATIONS

Kaler et al., Science 245:1371 (1989).
Madani & Kaler, Langmuir 6:125 (1990).
Hargreaves & Deamer, Biochem. 17:3759 (1978).
Search Report, files INSPEC, WPIL, Chem. Eng.

Primary Examiner—Robert L. Stoll
Assistant Examiner—John M. Covert
Attorney, Agent, or Firm—Connolly & Hutz

[57] ABSTRACT

The formation of spontaneous, thermodynamically stable vesicles from surfactant solutions is described. The vesicles comprise at least one single-chain, anionic surfactant and at least one single-chain cationic surfactant. Use of the vesicles in ultrafiltration treatment of water is disclosed.

16 Claims, 3 Drawing Sheets

Fig. 1A.
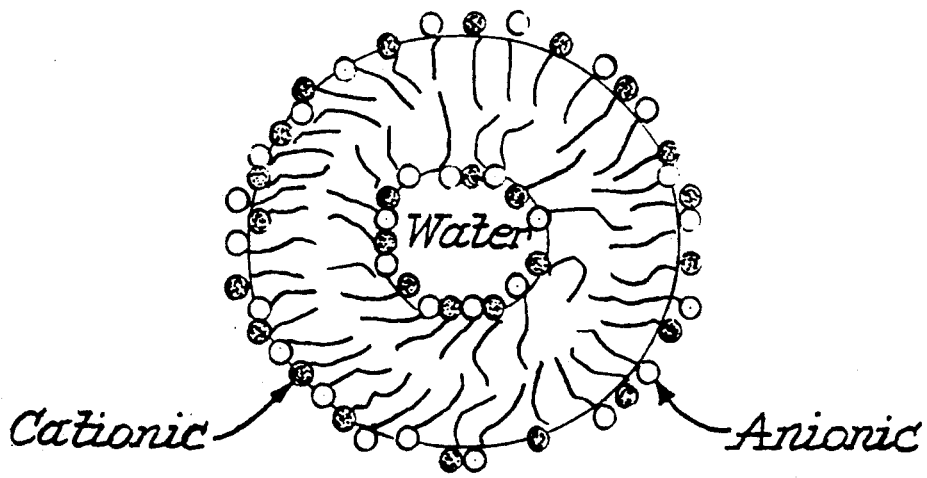
Cationic — Anionic
Fig. 1B.   Fig. 1C.
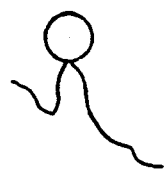 
Fig. 2.
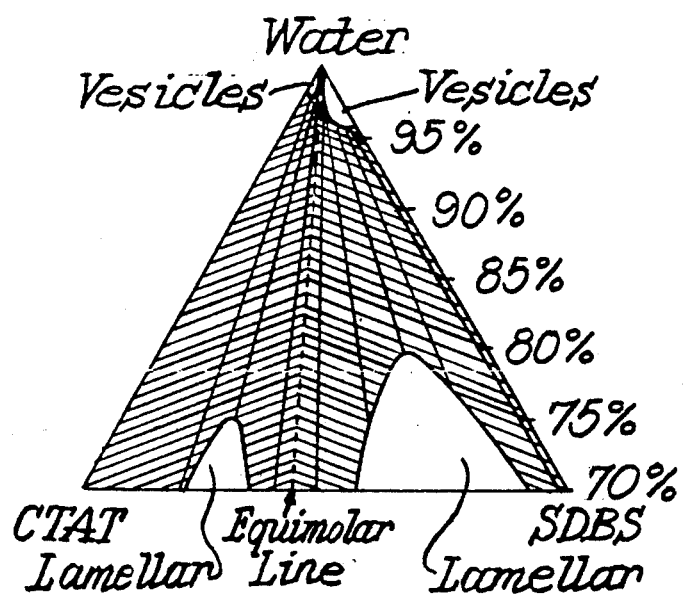

SPONTANEOUS EQUILIBRIUM SURFACTANT VESICLES

Pursuant to 35 U.S.C. §202(c), it is hereby acknowledged that the Government has certain rights in this invention, which was made in part with funds from the National Science Foundation.

FIELD OF THE INVENTION

The invention relates to surfactant vesicles. In particular, the invention relates to spontaneous, equilibrium vesicles containing an anionic surface active agent and a cationic surface active agent. The constituent surfactants are single-chain surfactants, i.e., the non-polar hydrocarbon region of the amphipathic surfactant molecules consists of a single hydrocarbon chain.

BACKGROUND OF THE INVENTION

Vesicles are single bilayer shells which are composed of amphipathic molecules such as surfactants or detergents. As used in this disclosure, the term vesicle will be understood as referring to unilamellar bilayer shells having a relatively small size, for example, having a diameter less than about 200 nanometers. The term "liposome" should be distinguished for purposes of this disclosure as referring to multilamellar shells which are generally larger in size, e.g. up to several microns in diameter.

Vesicles have a number of important utilities, including chemical and biochemical applications. For example, vesicles are useful in performing biochemical assays which involve the storage or encapsulation of biological materials such as enzymes or their substrates, which allows for controlled protection and release of an encapsulated substance. It is also possible to incorporate a reaction substrate into a vesicle membrane bilayer for presentation on the surface of the vesicle. Both vesicles and liposomes are of considerable interest in the controlled release and targeted delivery of pharmaceutically active agents. Loading of, for example, a medication, into vesicles or liposomes can serve to protect the load from degradation or dilution in the blood. Vesicles are also useful in preparing models for the study of photosynthesis and membrane phenomena, by incorporating the appropriate molecules into the vesicle membrane in order to induce electron transfers and/or establish proton gradients.

Vesicles and liposomes have conventionally been prepared using complex amphipathic molecules and/or elaborate preparation techniques. For example, liposomes may be composed of structurally complex phospholipids of the type which are found in natural membranes, such as phosphatidyl choline or phosphotidyl ethanolamine. Complex phospholipids normally contain more than one non-polar hydrocarbon "tail" region on each molecule. Liposomes formed therefrom can also incorporate other naturally-occurring membrane substances, for example steroids such as cholesterol or their analogs and derivatives, or can be modified by the presence of a surfactant or polymer.

Non-phospholipid vesicles have been prepared from various surfactants and detergents, but their preparation in aqueous solution has required considerable mechanical energy and/or elaborate chemical treatments. For example, it is known that vesicles may be prepared in aqueous solution using sonication or pressure filtration. Chemical treatments for inducing vesicle formation include detergent dialysis and reverse-phase evaporation. Vesicle solutions prepared by sonication are metastable, however, and the vesicles revert over time to more thermodynamically stable structures, such as multilamellar liquid-crystalline aggregates. See, generally, Madani and Kaler, *Langmuir* 6:125 (1990). In the course of vesicular breakdown, the contents of the vesicles are released.

A currently popular class of surfactant materials which have been used to prepare surfactant vesicles include polyoxyethylene esters, ethers, and amines. Exemplary disclosure is found in U.S. Pat. Nos. 4,217,334; 4,670,185; 4,743,449; 4,853,228; and 4,911,928.

It is known that many surfactants, and most simple detergents, are capable of forming micellar structures and emulsions in aqueous solution. Many surfactants are commercially important emulsifiers. Single-tailed amphiphiles, having relatively small tail groups and large head groups, invariably form micelles in solution.

In the past, addition of a cationic surfactant to an anionic micellar solution has been largely avoided. Solutions of anionic and cationic surfactants may form a lamellar phase, or may form precipitates, when combined in equimolar amounts. Although from theoretical considerations it could be predicted that amphiphilic molecules with relatively large hydrophobic groups and relatively small hydrophilic groups are capable of forming bilayer structures, spontaneous vesicle formation in vitro is in fact only rarely observed. Moreover, mixtures of simple anionic and cationic detergents are expected to produce mixed micelles in solution. See, Chen and Hall, *Colloid. Polym. Sci.* 251:41 (1973); Barker et al., *J. Chem. Soc. Faraday Trans.* 1 70:154 (1974); J. F. Scamehorn, Ed., *Phenomena in Mixed Surfactant Systems* (American Chemical Society, Washington, D.C. 1986).

There have been reports of spontaneous vesicle formation in certain mixtures of short- and long-chain, double-tailed lecithins. See Gabriel and Roberts, *Biochemistry*, 23:4011 (1984). Spontaneous vesicle formation has been reported to take place in solutions of double-tailed surfactants with hydroxide and other more exotic counterions. See Talmon et al., *Science* 221:1047 (1983); Brady et al., *J. Am. Chem. Soc.* 106:4279 (1984). Vesicle formation has been reported in some heated mixtures of anionic and cationic monoalkyl surfactants, but the vesicles were reported to be only transiently stable, and degenerated rapidly on cooling. See, Hargreaves and Deamer, *Biochemistry* 17:3759 (1978). Although these systems reflect improvements over conventional sonicated vesicles, the relatively restricted chemical or physical properties of the vesicles, or the limited availability of the constituent surfactants, were such that these methods have not been widely exploited.

SUMMARY OF THE INVENTION

Vesicles are prepared in aqueous solution from simple, single-chain surfactants. The vesicles contain at least one anionic surfactant and at least one cationic surfactant, and are formed spontaneously in solution by combining aqueous solutions of the anionic and cationic surfactants. The resulting vesicles are equilibrium vesicles, i.e., they are highly stable over time. The single-tailed, anionic surfactant preferably comprises an amphipathic molecule having a $C_8$ to $C_{18}$ hydrocarbon tail region and a hydrophilic, polar head group. The head group on the anionic surfactant is preferably selected from sulfonate, sulfate, carboxylate, benzene sulfonate and phosphate. The single-tailed, cationic surfactant preferably comprises an amphipathic molecule having a $C_8$ to $C_{18}$ hydrocarbon tail region and a hydrophilic polar head group. The head group on the cationic surfactant preferably comprises a quaternary ammonium group. The preferred single-chain surfactants are inexpensive and are readily available in bulk.

In accordance with various embodiments of the invention, the composition, size, shape, net surface charge, and permeability characteristics of the vesicles may be controlled by selecting the appropriate combinations and relative proportions of the anionic and cationic surfactants. In a further embodiment, water-soluble substances may be encapsulated within the interior, aqueous phase of the vesicles. Use of the vesicles of the invention in water purification and ultrafiltration is described.

BRIEF DESCRIPTION OF THE DRAWINGS

FIG. 1. (a) A schematic representation of a unilamellar vesicle prepared from an anionic surfactant and a cationic surfactant, wherein the open circles represent anionic polar moieties and the closed circles represent cationic polar moieties. (b) A schematic representation of a double-tailed, anionic surfactant molecule. (c) A schematic representation of the association between an anionic, single-chain surfactant molecule and a cationic, single-chain surfactant molecule.

FIG. 2. A CTAT-SDBS-water phase diagram at 25° C.

DETAILED DESCRIPTION OF THE INVENTION

Figure 3:
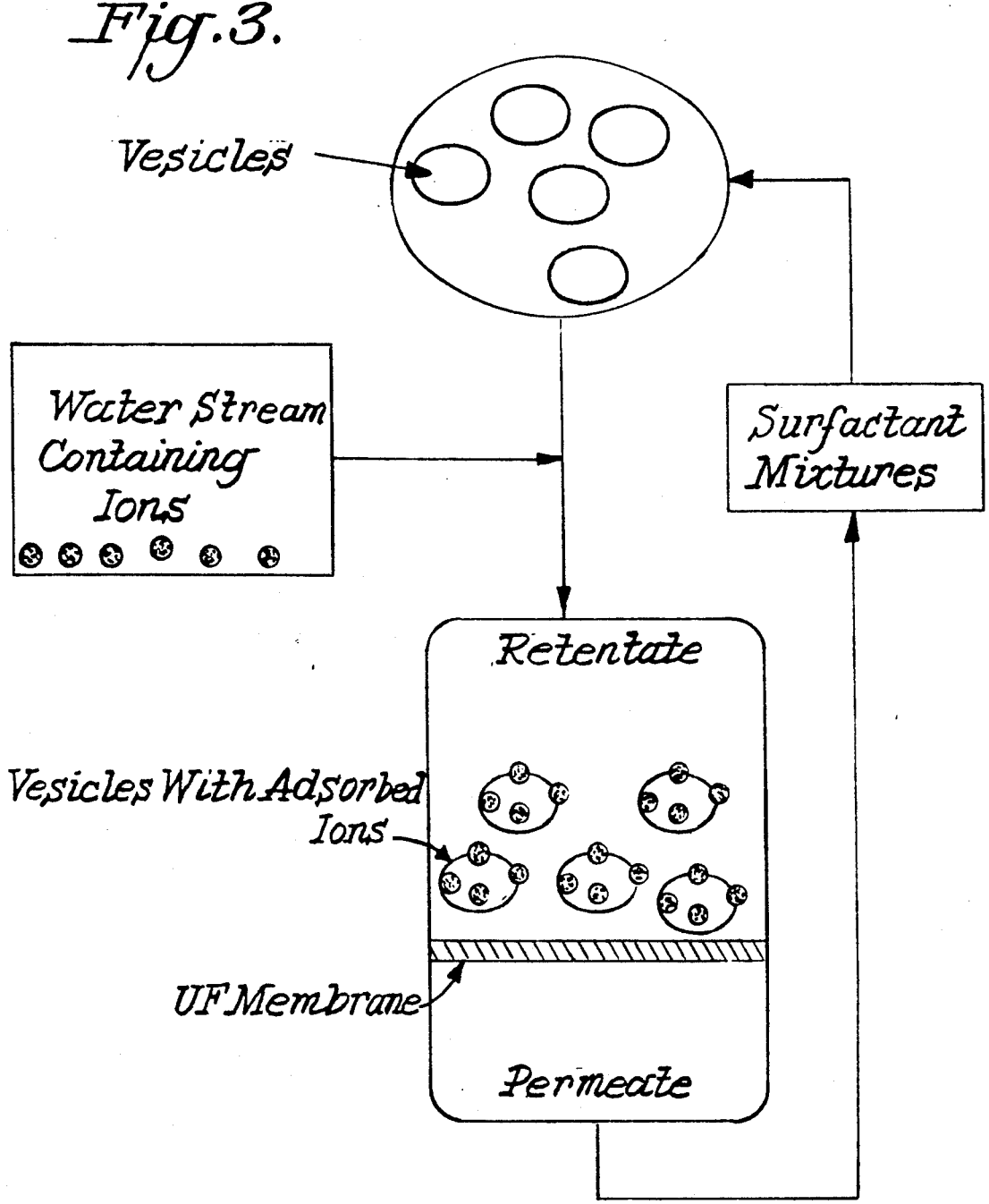
FIG. 3. A flow diagram representation of an embodiment of the invention wherein vesicles are used to purify water containing contaminant ions in an ultrafiltration process.

The vesicles in accordance with the invention are prepared from single-tailed, preferably monoalkyl, surfactants. As is known in the art, surfactants in general are a quite broad class of structurally diverse molecules. Surface active agents generally share common features; all surfactants are amphipathic molecules composed of one or more than one hydrophobic hydrocarbon region referred to as the "tail" region, and a hydrophilic, polar region referred to as the "head" region or head group. The amphipathic nature of these molecules is responsible for their behavior at and influence upon phase interfaces.

The single-tailed surface active agents useful in the practice of the invention are relatively simple molecules when viewed in the context of the broad array of known and available surface-active substances. The use of simple, readily available surfactants lends an economic attractiveness to the practice of the present invention.

A single-chain surfactant as contemplated by the invention is an amphipathic molecule having a single, hydrophobic tail region, and a single, polar head region. It is preferred that the hydrocarbon tail region of the surfactant molecule is aliphatic. Generally, the tail region of the surfactant molecule comprises a hydrocarbon chain having between 8 and 18 carbon atoms, which is preferably saturated, but may be unsaturated or substituted, provided that the essentially hydrophobic character of the tail region is preserved. When the length of the tail region exceeds about 18 carbon atoms, the temperature of the aqueous surfactant solution must often be increased to maintain solubility.

The charge of the polar head group determines the charge of the surface active agent. As described more fully herein, the vesicles of the invention are composed of at least one anionic surfactant and at least one cationic surfactant. Moieties comprising the polar head group in the anionic surfactant preferably include sulfonate, sulfate, carboxylate, benzene sulfonate, or phosphate. Moieties comprising the polar head group in suitable cationic surfactants include quaternary ammonium and pyridinium. Particularly preferred is trimethylammonium.

Exemplary cationic, single-chain surface active agents include alkyl trimethylammonium halides, alkyl trimethylammonium tosylates, and N-alkyl pyridinium halides.

Alkyl trimethylammonium halides include octyl trimethylammonium bromide, decyl trimethylammonium bromide, dodecyl trimethylammonium bromide, myristyl trimethylammonium bromide, and cetyl trimethylammonium bromide.

Alkyl trimethylammonium tosylates include octyl trimethylammonium tosylate, decyl trimethylammonium tosylate, dodecyl trimethylammonium tosylate, myristyl trimethylammonium tosylate, and cetyl trimethylammonium tosylate.

N-alkyl pyridinium halides include decyl pyridinium chloride, dodecyl pyridinium chloride, and cetyl pyridinium chloride.

Exemplary anionic, single-chain surface active agents include alkyl sulfates, alkyl sulfonates, alkyl benzene sulfonates, and saturated or unsaturated fatty acids and their salts.

Alkyl sulfates include sodium octyl sulfate, sodium decyl sulfate, sodium dodecyl sulfate, and sodium tetradecyl sulfate.

Alkyl sulfonates include sodium octyl sulfonate, sodium decyl sulfonate, and sodium dodecyl sulfonate.

Alkyl benzene sulfonates include sodium octyl benzene sulfonate, sodium decyl benzene sulfonate, and sodium dodecyl benzene sulfonate.

Fatty acid salts include sodium octanoate, sodium decanoate, sodium dodecanoate, and the sodium salt of oleic acid.

It will be understood that the above listings are representative rather than exhaustive. It will also be appreciated that many surfactants are available as polydisperse mixtures rather than as homogeneous preparations of a single surfactant species, and such mixtures are suitable for use in the invention.

The vesicles of the invention are characterized by their spontaneous formation in aqueous solution without the need for mechanical or chemical treatments. It has surprisingly been found that unilamellar vesicles are formed spontaneously upon combining an aqueous solution of a single-tailed, anionic surfactant with an aqueous solution of a single-tailed, cationic surfactant. Additionally, it has been found that the resulting vesicles are equilibrium vesicles, i.e., they are thermodynamically stable over extended time periods of up to one year. Certain preparations of vesicles so prepared have been found to be capable of withstanding freeze-thaw cycles without disruption or release of the contents.

In practice of the invention, aqueous solutions of the cationic and anionic surfactants are readily prepared from surfactant salts or by diluting concentrated surfactant solutions to the desired stock concentrations. A stock solution of the anionic surfactant is combined with a stock solution of the cationic surfactant, and the resulting reaction solution is gently mixed. Vesicles form immediately and spontaneously in the reaction solution upon combination of the stock solutions. The presence of vesicles in the resulting reaction solutions may be confirmed by, for example, quasi-elastic light scattering, freeze-fracture transmission electron microscopy, and glucose entrapment experiments. Vesicles in aqueous solution may be recovered or concentrated using filtration or centrifugation.

It will be appreciated that this method of vesicle preparation allows for gentle yet efficient encapsulation of an aqueous phase to take place as the surfactant stock solutions are combined without mechanical or chemical perturbations from the final vesicle composition or structure. Encapsulation refers to incorporation of material into the aqueous phase within the interior of the vesicle space as the vesicles are formed and the storage of the material within the vesicle structure. Water-soluble substances are effectively encapsulated within the vesicles by incorporating the substance to be encapsulated into the anionic and/or the cationic surfactant stock solution before the solutions are combined in the reaction solution. Examples of materials which may be encapsulated in this manner into vesicles include dyes, sugars, pharmaceuticals and components of cosmetics and detergents.

Although the molecular interactions involved in spontaneous vesicle formation from mixtures of single-tail anionic and cationic surfactants have not been fully characterized, it is believed that individual molecules of the cationic and anionic surfactants may associate and form an amphoteric entity which mimics the action of a double-tailed surfactant. This presumptive association of molecules is represented in FIG. 1(c) and may be compared to the structure of a conventional, double-tailed surfactant shown in FIG. 1(b). In the context of an equilibrium vesicle of the type herein described, which is ideally represented in FIG. 1(a), each individual surfactant molecule is likely to be associated with more than one neighboring molecule.

In preparing the equilibrium vesicles, a net negative or net positive charge may be imparted to the membrane surface of the vesicles. If a larger proportion of the total surfactant in the final vesicles is the anionic surfactant species, the vesicle surface will have a net negative charge, the magnitude of which may be precisely controlled. Negatively-charged vesicles are prepared by increasing the amount of anionic surfactant relative to the amount of cationic surfactant in the reaction solution, either by adding a greater volume of the anionic solution or by adding a more concentrated anionic solution. The magnitude of the negative surface charge on the final vesicles will vary depending upon the amount by which the anionic surfactant species is greater in abundance than the cationic surfactant species in the reaction solution. Conversely, a net positive charge may be imparted to the surfaces of the vesicles by adding the cationic species in excess of the anionic species. Obtaining a desired surface charge on the membrane of the vesicles may thus be achieved by controlling the relative proportions of anionic and cationic surfactant.

The size and curvature properties (shape) of the vesicles can vary depending upon the length of the hydrocarbon tail regions of the constituent surfactants and the nature of the polar head groups. In general, the diameter size of the vesicles is between 10 and 250 nanometers, usually between 30 and 150 nm. A degree of control over vesicle size may be achieved by selecting the relative lengths of the hydrocarbon tail regions of the anionic and cationic surfactants. It has been noted that the largest vesicles, reaching up to 150 to 200 nanometers in diameter, are achieved when there is disparity between the length of the hydrocarbon tail on the anionic surfactant and the hydrocarbon tail on the cationic surfactant. For example, large vesicles are observed when a $C_{16}$ cationic surfactant solution is combined with a $C_8$ anionic surfactant solution. Substantially smaller vesicles are produced as the lengths of the hydrocarbon tails on the anionic and cationic surfactant species are more closely matched. The permeability characteristics of the vesicles are also related to the nature of the constituent surfactants, particularly to the chain length of the hydrocarbon tail regions of the surfactants. Generally, longer tail lengths on the surfactant molecules will decrease the permeability of the vesicles by increasing the thickness and hydrophobicity of the vesicle membranes. Control of reagent and substrate permeation across the vesicle membranes can be a significant parameter when using the vesicles as microreactors.

The ratio of cationic to anionic molecules in the vesicles of the invention may vary within broad limits while maintaining the features of stability and spontaneous formation. Vesicles have been characterized which have an anionic surfactant to cationic surfactant ratio ranging between 1:9 and 9:1. The vesicle charge and size, and other vesicle characteristics, vary considerably over this range. It is noted that combining equimolar amounts of anionic surfactant and cationic surfactant as stock solutions can result in formation of insoluble precipitates or undesirable lamellar structures. Hence, under most circumstances, a 1:1 molar ratio of anionic to cationic surfactant should be avoided.

Unilamellar equilibrium vesicles prepared in accordance with the invention find utility in the same general applications as conventional sonicated vesicles and vesicles prepared from more elaborate, expensive surfactants. For example, the vesicles are useful as model membranes, as capsules for various agents in assays and drug delivery, as microreactors, and as substrates for enzymes and proteins.

A further important utility for the vesicles is in the field of water purification and cleaning. Of particular interest is the enhancement of separation processes such as ultrafiltration.

Ultrafiltration is a membrane process capable of retaining solutes as small as 10 angstrom while passing solvent and smaller solutes. Ultrafiltration is commonly applied to aqueous streams which contain soluble contaminants such as macromolecules, colloids, salts, sugars or polyvalent metal ions. The ultrafiltration technique is used to concentrate or fractionate, often simultaneously, and is practiced both in the laboratory and on a large scale industrially. See, e.g., Handbook of Separation Techniques for Chemical Engineers, McGraw Hill: New York (1979); Ultrafiltration Membranes and Applications, A. R. Cooper (Ed.), Plenum: New York (1979). Ultrafiltration membranes are usually polymeric and seldom exhibit 100% retention for any species near their rated pore size, because the pore size of the polymeric membranes is not controllable within narrow limits. Accordingly, the standard pore size rating or molecular weight cutoff of ultrafiltration membranes is defined as the molecular weight of globular protein that is 90% retained. The lowest molecular weight cutoff generally attainable in standard ultrafiltration membranes is about 300 daltons, which corresponds to a pore size of about 10 angstrom. Small ions, such as sodium or chloride ions, that pass through the ultrafiltration membranes may be retained by reverse osmosis membranes. Compared to ultrafiltration, however, reverse osmosis is a relatively high pressure process. Recently, a new method known as Micellar Enhanced Ultrafiltration has been introduced to remove solutes of molecular weight less than 300 daltons by ultrafiltration. See, e.g., *Surfactant-Based Separation Processes*, Marcel Dekker: New York (1989); *Surfactants in Chemical/Process Engineering*, Marcel Dekker: New York (1988). This method involves the use of surfactant micelles, whose radii are generally in the range of 25 to 100 angstrom (2.5-10 nm). The micelles are capable of solubilizing low molecular weight organic solutes in their interior core and absorbing multivalent ions on their charged surface. The resulting larger aggregates can be filtered through a high molecular weight cutoff membrane with a higher flux, flux being the measure of a membrane's productivity. The higher the flux at a given selectivity, the more economical and efficient is the separation process.

A major improvement in flux in ultrafiltration processes can be achieved utilizing the spontaneous vesicles of the invention. The size of the vesicles are more than an order of magnitude larger than the size of the micelles used in Micellar Enhanced Ultrafiltration. This facilitates the use of ultrafiltration membranes with larger pore diameters in separations which involve low molecular weight solutes.

An exemplary ultrafiltration process is shown as a flow diagram in FIG. 3. As shown therein, a solution of spontaneous vesicles prepared from aqueous solutions of anionic and cationic surfactants as described herein are combined with a waste water stream containing ions such as multivalent metal ions or organic anions. The ions are readily adsorbed onto the surface of the vesicles. The vesicles and charged contaminants aggregated thereon are efficiently retained by an ultrafiltration membrane, designated "UF Membrane" in the Figure. The contaminants are thus held in the retentate with the vesicles, while the permeate can be reused in the preparation of vesicles.

Figure 4:
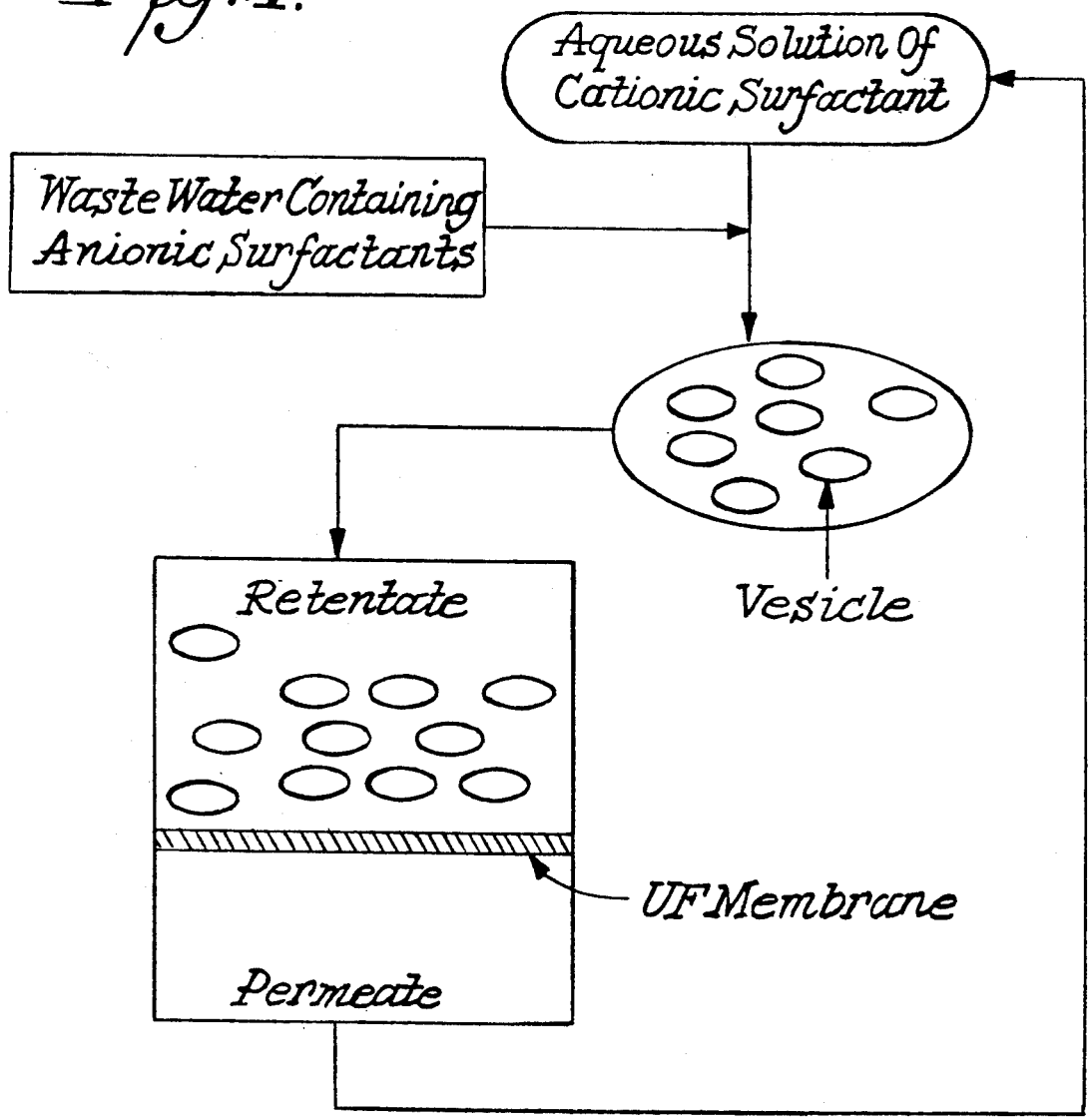
FIG. 4. A flow diagram representation of a further embodiment of the invention wherein vesicles are used to purify water containing a contaminant surfactant in an ultrafiltration process.

In another water treatment scheme, shown in FIG. 4, a wastewater to be treated contains surfactants. For example, the stream of waste water may contain anionic surfactants. The wastewater is combined with an oppositely charged ionic (cationic) surfactant solution to form large aggregate structures such as vesicles by the electrostatic attraction between the two oppositely-charged surfactants. The aggregates are thus formed in situ in the wastewater, and are efficiently retained by ultrafiltration membranes. Hence, the use of vesicles and vesicle solutions as described in this disclosure can greatly enhance the flux during ultrafiltration of extremely small solutes.

The following examples serve to illustrate the practice of a preferred embodiment of the invention, wherein the cationic surfactant comprises cetyl trimethylammonium tosylate (CTAT) and the anionic surfactant comprises sodium dodecylbenzene sulfonate (SDBS). The following examples are illustrative only and should not be construed as limiting the scope of the invention.

EXAMPLE 1

Different stock solutions of both SDBS and CTAT of known concentration were prepared in deionized water. Stock solutions were equilibrated at the temperature of interest, and gentle mixing of anionic and cationic solutions resulted in the spontaneous formation of vesicles. Except for gentle mixing, the solutions were not subjected to any type of mechanical agitation. When a sample in the two-phase region was prepared, phase separation was occasionally accelerated by centrifugation of the sample at 400 g. High-performance liquid chromatography was used to determine the ratio of tosylate and dodecylbenzene ion concentrations, a sodium ion-specific electrode to determine the concentration of sodium ions, and Karl Fisher titration to determine the water concentration. FIG. 2 shows a CTAT-SDBS-water phase diagram of the reaction mixtures at 25° C. As seen in FIG. 2, two distinct one-phase regions containing vesicles are present in the water-rich corner. The two-phase regions are cross-hatched, and the tie-lines were determined experimentally. There was no evidence of a (first-order) micelle-vesicle phase transition as either of the micellar phases on the surfactant-water edges of the triangle is titrated against a micellar solution of the other surfactant. If any micelle-vesicle two-phase regions existed, they were vanishingly small.

A spectrometer of standard design was used for the quasi-elastic light scattering (QLS) measurements. Solutions for light scattering were gravity filtered through a 0.22 micron Millipore filter into the scattering cell. All measurements were done at a scattering angle of 90°, and the intensity autocorrelation function was analyzed by the method of cumulants. See, Koppel, *J. Chem. Phys.* 57:4814 (1972). Measurements were made of vesicles in both the CTAT-rich and the SDBS-rich one-phase regions and the results are shown in the following Table 1. As will be observed from Table 1 and FIG. 2, vesicle phases are present in highly dilute solutions.

TABLE 1

| Water (%) | CTAT/SDBS | Radius (A) |
|---|---|---|
| | One-phase region | |
| 99.7 | 2/8 | 330 |
| | 3/7 | 340 |
| | 4/6 | 450 |
| | 5/5 | 720 |
| | 6/4 | 500 |
| | 7/3 | 570 |
| | 8/2 | 610 |
| | 9/1 | 580 |
| 99.0 | 1/9 | 430 |
| | 3/7 | 350 |
| 98.0 | 2/8 | 300 |
| | 8/2 | 560 |
| 97.0 | 1/9 | 470 |
| | 3/7 | 540 |
| | Two-phase region | |
| 95.0 | 1/9 | 550 |
| 93.0 | 1/9 | 720 |
| 91.0 | 1/9 | 830 |

Samples in the CTAT-rich regions were in general more turbid than those in the SDBS-rich region, a result consistent with the presence of larger vesicles. It will be noted that the apparent vesicle size increases as the water content decreases at a constant SDBS/CTAT ratio, although no accounting of the effect of interparticle interactions on apparent size was attempted. The average vesicle radius was between 30 and 80 nm, and there was substantial size polydispersity, as manifested by large values of the variance (between 0.1 and 0.2), which is related to the second cumulant. The vesicles are charged, with SDBS-rich vesicles migrating toward the anode of an electrophoresis cell and CTAT-rich vesicles moving toward the cathode.

The presence of vesicles was further confirmed, and their size ranges observed, by transmission electron microscopy. Samples for electron microscopy were prepared using standard preparation procedures. Specifically, a thin layer (less than 50 micrometers) of the vesicle dispersion was sandwiched between two copper planchettes (RMC, Tuscon, Ariz.). The sample sandwiches were frozen by placing them between opposite jets of liquid propane cooled by liquid nitrogen to −190° C. in a Gilkey-Staehelin jet freeze device (RMC, Tuscon, Ariz.). The specimens were transferred under liquid nitrogen to a Reichert Jung Cryofract 190 freeze-fracture device (Cambridge Instruments Inc., Buffalo, N.Y.), fractured at −170° C. and $10^{-9}$ torr, and immediately replicated with 1.0 nm of platinum-carbon alloy applied by electron-beam evaporation at a 45° angle to the fracture surface, followed by the imposition of a 15-nm-thick reinforcing film of carbon, applied at normal incidence. In the TEM images (JEOL 100 CX-II; 80 kV; initial magnification, ×40,000) shadows appear light. Vesicle size distributions were obtained by measuring the diameters of vesicles that showed well-defined shadows, indicating that the fracture surface propagated near the center of the vesicle.

When viewed by electron microscopy, the CTAT-rich vesicle dispersion showed a rather polydisperse size distribution with diameters ranging from about 10 nm to more than 250 nm. The average diameter was about 70 nm. The vesicles were uniformly distributed throughout the sample, indicative of good freezing. No multilamellar vesicles were seen in this sample or in an SDBS-rich sample, although sometimes a small vesicle was observed embedded within a larger vesicle. The size distribution of the SDBS-rich vesicle dispersion sample was significantly narrower than that of the CTAT-rich dispersion, with an average diameter of about 60 nm. There appeared to be fewer large vesicles (>200 nm diameter) in the SDBS-rich dispersion than in the CTAT-rich dispersion. The number density of the SDBS vesicles appeared to be greater than in the CTAT-rich fraction.

EXAMPLE 2

Entrapment of a water-soluble solute within the vesicles of the invention was carried out as follows. Samples for trapping experiments were prepared as described in connection with Example 1 with the substitution of a 0.3M glucose solution for water. Vesicles formed in the presence of glucose were found to be comparable in size to those formed in deionized water. The glucose-containing vesicles (1.5 ml) were placed in a dialysis bag (Spectrapor standard cellulose tubing) and dialyzed against 500 ml of isotonic salt (0.075M KCl and 0.075M NaCl). Four dialyzate changes at 3-hour intervals were sufficient to quantitavely remove the glucose from the exterior of the vesicles as determined by the change in absorbence at 340 nm due to the formation of the reduced form of nicotinamide adenine dinucleotide phosphate in the presence of glucose-6-phosphate dehydrogenase and hexokinase. See, Demel et al. *Biochem. Biophys. Acta* 150:665 (1968). Triton X-100 was then added to the sample in the dialysis bag to disrupt the vesicles and release the entrapped glucose. Disrupted vesicles were dialyzed for 3 hours, and assay of the dialyzate showed the presence of substantial glucose. There was some slight interference by the anionic surfactant with the kinetics of the enzymatic reaction.

While the invention has been described in the above disclosure and examples in terms of the currently preferred embodiments, obvious variations would be apparent to those skilled in the art. The specific surfactant combinations needed to obtain optimum vesicle characteristics such as size, charge, or permeability for a particular use may be determined empirically. It is also within the scope of the invention to utilize mixtures of different anionic surfactants and/or cationic surfactants in preparing the vesicles. It would further be expected that minor amounts of other water-soluble and/or lipid soluble materials could be added to the stock solutions, and incorporated into the final vesicles, without impairing spontaneous vesicle formation in solution or substantially altering the stability properties of the resulting vesicles. For example, certain nonionic surfactants, charge-producing amphiphiles, sterols, or other natural or synthetic membrane materials may be incorporated into the vesicles to modify the vesicle properties, provided that such materials are used in quantities which do not inhibit the formation of vesicles in solution. It is also contemplated that the surfactants comprising the vesicles of the invention may consist of monomers which are polymerizable in the context of the assembled vesicle to yield polymer-coated vesicles of reduced permeability.

What is claimed is:

1. Unilamellar equilibrium vesicles comprising at least one anionic, single chain surface active agent and at least one cationic, single chain surface active agent, the vesicles characterized by a unilamellar bilayer structure, thermodynamic stability, and stability to temperature change, each of said surface active agents having a polar head region and a hydrophobic tail region of not more than 18 carbon atoms.

2. Unilamellar equilibrium vesicles as claimed in claim 1 wherein said anionic surface active agent includes an aliphatic hydrocarbon tail region having between about 8 and 18 carbon atoms and a polar head region consisting of a group selected from sulfonate, sulfate, carboxylate, benzene sulfonate, and phosphate, and said cationic surface active agent includes an aliphatic hydrocarbon tail region having between about 8 and 18 carbon atoms and a polar head region consisting of a group selected from quaternary ammonium and pyridinium.

3. Unilamellar equilibrium vesicles as claimed in claim 1, wherein the aliphatic hydrocarbon tail region of each of the anionic and cationic surfactants consists of a saturated alkyl moiety.

4. Unilamellar equilibrium vesicles as claimed in claim 1 having a diameter size of between about 30 and 150 nanometers.

5. Unilamellar equilibrium vesicles as claimed in claim 1 having a mean diameter size of less than 200 nanometers.

6. Unilamellar equilibrium vesicles as claimed in claim 1 having a water-soluble substance encapsulated therein.

7. Unilamellar equilibrium vesicles as claimed in claim 1 wherein the surfaces of the vesicles have a net negative charge.

8. Unilamellar equilibrium vesicles as claimed in claim 1 wherein the surfaces of the vesicles have a net positive charge.

9. A process for forming spontaneous unilamellar equilibrium vesicles in aqueous solution, comprising the steps of:
 a) providing an aqueous solution of at least one anionic, single chain surface active agent;
 b) providing an aqueous solution of at least one cationic, single chain surface active agent;
 c) combining the aqueous solutions from steps a) and b) to spontaneously form an aqueous solution containing vesicles without the addition of heat or mechanical agitation.

10. The method of claim 9 comprising the further step of recovering the aqueous vesicles formed in the reaction solution.

11. The process as claimed in claim 9, wherein the net surface charge of the vesicles formed in the reaction solution is controlled by adjusting the relative amounts or concentrations of the anionic and cationic surfactant solutions added to the reaction solution.

12. The process as claimed in claim 9, wherein the size of the vesicles formed in the reaction solution is controlled by selection of the length of the hydrocarbon tail region on one or both of the anionic or the cationic surface active agents.

13. The process as claimed in claim 9 wherein the membrane permeability characteristics of the vesicles formed in the reaction solution are controlled by selection of the length of the hydrocarbon tail region on one or both of the anionic or the cationic surface active agents.

14. The process as claimed in claim 9 wherein the aqueous solution of one or both of the anionic or the cationic surface active agent additionally contains a water-soluble substance, which substance is encapsulated in an aqueous phase in the vesicles as they are formed.

15. Unilamellar equilibrium vesicles as claimed in claim 1 containing non-equimolar amounts of the anionic, single chain surfactant and the cationic, single chain surfactant.

16. Unilamellar equilibrium vesicles produced by the process as claimed in claim 9.

* * * * *